(12) United States Patent
Chee et al.

(10) Patent No.: US 7,045,512 B2
(45) Date of Patent: May 16, 2006

(54) FUNGICIDAL PHENOXYPHENYLHYDRAZINE DERIVATIVES

(75) Inventors: Gaik-Lean Chee, Guelph (CA); Mark A. Dekeyser, Waterloo (CA); Kenneth W. Seebold, Jr., Tifton, GA (US); Ewa Maria Osika, Cambridge (CA); Walter G. Brouwer, Glasgow (GB); Sheldon B. Park, Guelph (CA); Hoi Kiong Lai, Guelph (CA)

(73) Assignees: Uniroyal Chemical Company, Inc., Middlebury, CT (US); Crompton Co./Cie, Elmira (CA)

( * ) Notice: Subject to any disclaimer, the term of this patent is extended or adjusted under 35 U.S.C. 154(b) by 0 days.

(21) Appl. No.: 10/855,452

(22) Filed: May 27, 2004

(65) Prior Publication Data

US 2004/0266738 A1 Dec. 30, 2004

Related U.S. Application Data

(60) Provisional application No. 60/482,524, filed on Jun. 24, 2003.

(51) Int. Cl.
C07C 243/28 (2006.01)
C07C 245/06 (2006.01)
C07D 213/63 (2006.01)
C07D 249/08 (2006.01)
A01N 47/12 (2006.01)

(52) U.S. Cl. ............ 514/150; 514/346; 514/383; 514/485; 514/486; 514/639; 534/885; 546/306; 548/266.8

(58) Field of Classification Search ........... 534/885; 546/306; 548/266.8; 564/251, 310; 514/346, 514/383, 485, 486, 639, 150
See application file for complete search history.

(56) References Cited

U.S. PATENT DOCUMENTS 4,816,373 A * 3/1989 Ohashi et al. ............ 430/264

FOREIGN PATENT DOCUMENTS

| EP | 1178035 A1 | 6/2002 |
|----|------------|--------|
| EP | 1178039 A1 | 6/2002 |
| GB | 1160648    | * 8/1969 |

OTHER PUBLICATIONS

Bar et al. ,Chemical Abstracts, 93:238954, 1980.*
Zhang et al., Tetrahedron Letters, 41(17), 3025-3028, 2000.*

* cited by examiner

Primary Examiner—Fiona T. Powers
(74) Attorney, Agent, or Firm—Daniel Reitenbach

(57) ABSTRACT

A fungicidally active compound of the formula:
a)

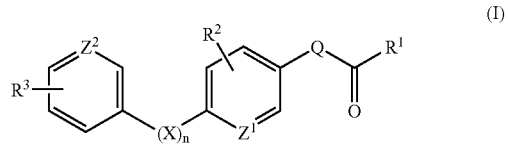

(I)

wherein
Q is —NY—NH—, —N=N—, or

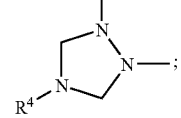

X is oxygen, sulfur, sulfoxide, or sulfone;
n is 0 or 1;
Y is hydrogen, $C_1$–$C_4$ alkanoyl, $C_1$–$C_4$ haloalkanoyl, $C_1$–$C_6$ straight chain or branched alkoxycarbonyl, $C_1$–$C_4$ alkoxy($C_1$–$C_4$)alkoxycarbonyl, $C_1$–$C_4$ alkyl, or $C_1$–$C_4$ haloalkyl;
$R^1$ is $C_1$–$C_6$ alkoxy, $C_3$–$C_6$ branched alkoxy, $C_3$–$C_6$ cycloalkoxy, phenoxy, benzyloxy, $C_2$–$C_6$ alkenyloxy, $C_2$–$C_6$ alkynyloxy, $C_1$–$C_6$ haloalkoxy, silyloxy, ($C_1$–$C_6$ alkoxy)-carbonylmethoxy, $C_1$–$C_6$ thioalkoxy, $C_1$–$C_6$ alkylamino, $C_1$–$C_6$ alkyl, $C_3$–$C_6$ branched alkyl, ($C_1$–$C_6$ alkoxy) $C_1$–$C_6$ alkoxy, or ($C_1$–$C_6$ alkoxy)carbonyl;
$R^2$ and $R^3$ are each, independently, hydrogen, halogen, $C_1$–$C_6$ alkyl, $C_3$–$C_6$ branched alkyl, $C_1$–$C_6$ haloalkyl, $C_1$–$C_6$ alkoxy, $C_1$–$C_6$ haloalkoxy, cyano, or ($C_1$–$C_6$ alkoxy)carbonyl;
$R^4$ is $C_1$–$C_6$ alkyl; and
$Z^1$ and $Z^2$ are each independently, carbon or nitrogen, with the proviso that when $Z^1$ is carbon, X is oxygen, and $R^2$ is hydrogen, then $R^3$ cannot be hydrogen;
b)

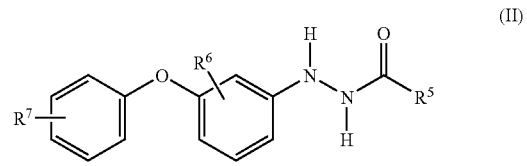

(II)

wherein $R^5$ is $C_1$–$C_6$ alkoxy; and $R^6$ and $R^7$ are, independently, halo or $C_1$–$C_6$ haloalkyl; or
c)

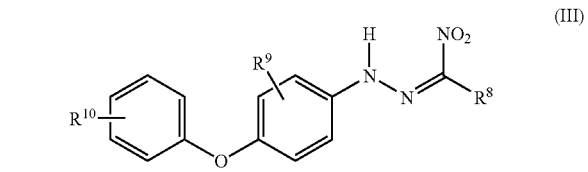

(III)

wherein $R^8$ is $C_1$–$C_6$ alkyl; and $R^9$ and $R^{10}$, independently, are halo or $C_1$–$C_6$ haloalkyl.
and a method for controlling fungi using the compound.

14 Claims, No Drawings

FUNGICIDAL PHENOXYPHENYLHYDRAZINE DERIVATIVES

FUNGICIDAL PHENOXPHENYLHYDRAZINE DERIVATIVES

This application claims benifit of Provisional U.S. Application No. 60/482,524 filed Jun. 24, 2003.

FIELD OF THE INVENTION

This invention relates to certain fungicidal phenoxyphenylhydrazine derivatives. This invention also relates to a method for controlling fungi using the phenoxyphenylhydrazine derivatives.

BACKGROUND OF THE INVENTION

U.S. Pat. No. 5,367,093 describes phenylhydrazine derivative compounds useful as insecticides, acaricides and nematocides.

U.S. Pat. No. 6,297,275 describes a method for controlling fungi using phenylhydrazine derivatives.

EP 1178035 A1 describes certain fungicidal phenylimine derivatives.

EP 1178039 A1 describes certain fungicidal phenylthioureas and phenylthiocarbamates.

It is an object of this invention to provide novel phenoxyphenylhydrazine derivative compounds and compositions.

It is a further object of this invention to provide a method for controlling fungi using the phenoxyphenylhydrazine derivative compounds and compositions.

SUMMARY OF THE INVENTION

This invention relates to a phenoxyphenylhydrazine compound of the formula:

a)

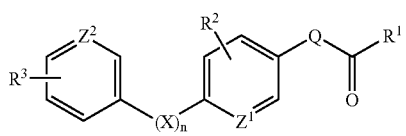
(I)

wherein
Q is —NY—NH—, —N=N—, or

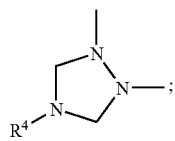

X is oxygen, sulfur, sulfoxide, or sulfone;
n is 0 or 1;
Y is hydrogen, $C_1$–$C_4$ alkanoyl, $C_1$–$C_4$ haloalkanoyl, $C_1$–$C_6$ straight chain or branched alkoxycarbonyl, $C_1$–$C_4$ alkoxy ($C_1$–$C_4$)alkoxycarbonyl, $C_1$–$C_4$ alkyl, or $C_1$–$C_4$ haloalkyl;
$R^1$ is $C_1$–$C_6$ alkoxy, $C_3$–$C_6$ branched alkoxy, $C_3$–$C_6$ cycloalkoxy, phenoxy, benzyloxy, $C_2$–$C_6$ alkenyloxy, $C_2$–$C_6$ alkynyloxy, $C_1$–$C_6$ haloalkoxy, silyloxy, ($C_1$–$C_6$ alkoxy)-carbonylmethoxy, $C_1$–$C_6$ thioalkoxy, $C_1$–$C_6$ alkylamino, $C_1$–$C_6$ alkyl, $C_3$–$C_6$ branched alkyl, ($C_1$–$C_6$ alkoxy) $C_1$–$C_6$ alkoxy, or ($C_1$–$C_6$ alkoxy)carbonyl;
$R^2$ and $R^3$ are each, independently, hydrogen, halogen, $C_1$–$C_6$ alkyl, $C_3$–$C_6$ branched alkyl, $C_1$–$C_6$ haloalkyl, $C_1$–$C_6$ alkoxy, $C_1$–$C_6$ haloalkoxy, cyano, or ($C_1$–$C_6$ alkoxy)carbonyl;
$R^4$ is $C_1$–$C_6$ alkyl; and
$Z^1$ and $Z^2$ are each independently, carbon or nitrogen,
with the proviso that when $Z^1$ is carbon, X is oxygen, and $R^2$ is hydrogen, then $R^3$ cannot be hydrogen;

b)

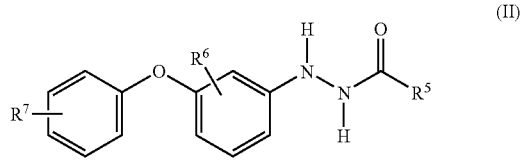
(II)

wherein $R^5$ is $C_1$–$C_6$ alkoxy; and $R^6$ and $R^7$ are, independently, halo or $C_1$–$C_6$ haloalkyl; or c)

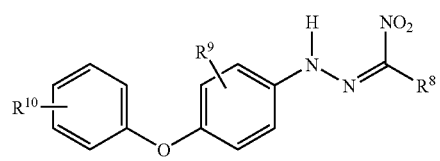

wherein $R^8$ is $C_1$–$C_6$ alkyl; and $R^9$ and $R^{10}$, independently, are halo or $C_1$–$C_6$ haloalkyl.

This invention also relates to a method for controlling fungi, particularly phytopathogenic fungi, comprising contacting the fungi with a fungicidally effective amount of a phenoxyphenylhydrazine compound of the formula:

a)

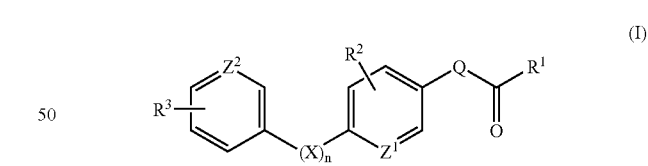
(I)

wherein Q, X, n, Y, $Z^1$, $Z^2$, and $R^1$–$R^4$ are as defined above;

b)

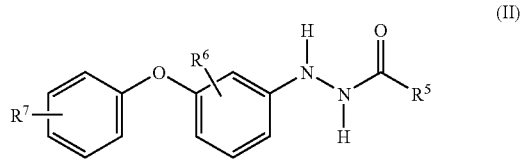
(II)

wherein $R^5$, $R^6$, and $R^7$ are as defined above; or c)

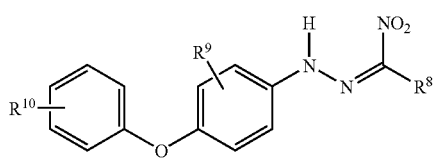

wherein $R^8$, $R^9$ and $R^{10}$ are as defined above.

DETAILED DESCRIPTION OF THE INVENTION

This invention relates to a phenoxyphenylhydrazine compound of the formula:

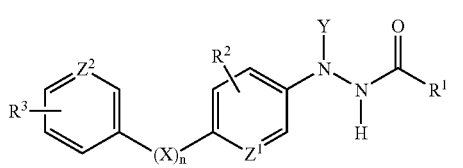

(IA)

or

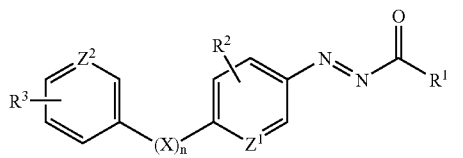

(IB)

or

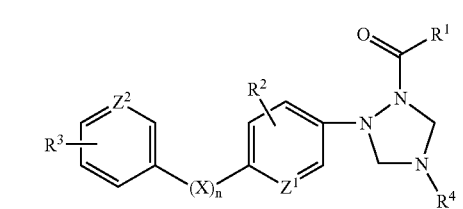

(IC)

wherein X, n, Y, $Z^1$, $Z^2$, and $R^1$–$R^4$ are as defined above.
Preferably, Q is —NY—NH—, —N=N—, or

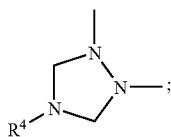

X is oxygen, sulfur, sulfoxide, or sulfone;
n is 0 or 1;
Y is hydrogen, $C_1$–$C_4$ alkanoyl, $C_1$–$C_4$ haloalkanoyl, $C_1$–$C_6$ straight chain or branched alkoxycarbonyl, $C_1$–$C_4$ alkoxy ($C_1$–$C_4$)alkoxycarbonyl, $C_1$–$C_4$ alkyl, or $C_1$–$C_4$ haloalkyl;
$R^1$ is $C_1$–$C_6$ alkoxy, $C_3$–$C_6$ branched alkoxy, $C_3$–$C_6$ cycloalkoxy, phenoxy, benzyloxy, $C_2$–$C_6$ alkenyloxy, $C_2$–$C_6$ alkynyloxy, $C_1$–$C_6$ haloalkoxy, silyloxy, ($C_1$–$C_6$ alkoxy)carbonylmethoxy, $C_1$–$C_6$ thioalkoxy, $C_1$–$C_6$ alkylamino, $C_1$–$C_6$ alkyl, $C_3$–$C_6$ branched alkyl, ($C_1$–$C_6$ alkoxy) $C_1$–$C_6$ alkoxy, or ($C_1$–$C_6$ alkoxy)carbonyl;

$R^2$ and $R^3$ are each, independently, hydrogen, halogen, $C_1$–$C_6$ alkyl, $C_3$–$C_6$ branched alkyl, $C_1$–$C_6$ haloalkyl, $C_1$–$C_6$ alkoxy, $C_1$–$C_6$ haloalkoxy, cyano, or ($C_1$–$C_6$ alkoxy)carbonyl;
$R^4$ is $C_1$–$C_6$ alkyl; and
$Z^1$ and $Z^2$ are each independently, carbon or nitrogen, with the proviso that when $Z^1$ is carbon, X is oxygen, and $R^2$ is hydrogen, then $R^3$ cannot be hydrogen;
More preferably, Q is —NY—NH—, —N=N—, or

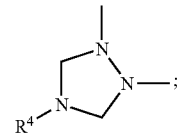

X is oxygen, sulfur, sulfoxide, or sulfone, most preferably oxygen;
n is 0 or 1, most preferably 1;
Y is hydrogen, $C_1$–$C_4$ haloalkanoyl, most preferably hydrogen;
$R^1$ is $C_1$–$C_6$ alkoxy, $C_3$–$C_6$ branched alkoxy, $C_1$–$C_6$ haloalkoxy, silyloxy, most preferably $C_1$–$C_6$ alkoxy or $C_3$–$C_6$ branched alkoxy;
$R^2$ and $R^3$ are each, independently, hydrogen, halogen, $C_3$–$C_6$ branched alkyl, $C_1$–$C_6$ haloalkyl, $C_1$–$C_6$ haloalkoxy, or ($C_1$–$C_6$ alkoxy)carbonyl, most preferably halogen, $C_3$–$C_6$ branched alkyl, $C_1$–$C_6$ haloalkyl;
$R^4$ is $C_1$–$C_6$ alkyl; and
$Z^1$ and $Z^2$ are each independently, carbon or nitrogen, most preferably carbon;
with the proviso that when $Z^1$ is carbon, X is oxygen, and $R^2$ is hydrogen, then $R^3$ cannot be hydrogen;
This invention also relates to a phenoxyphenylhydrazine compound of the formula:

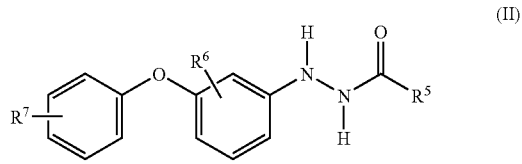

(II)

wherein $R^5$ is $C_1$–$C_6$ alkoxy; and $R^6$ and $R^7$ are, independently, halo or $C_1$–$C_6$ haloalkyl; or

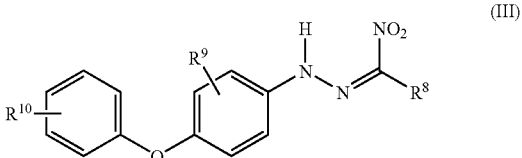

(III)

wherein $R^8$ is $C_1$–$C_6$ alkyl; and $R^9$ and $R^{10}$, independently, are halo or $C_1$–$C_6$ haloalkyl.

Preferably, $R^5$ is $C_1$–$C_6$ alkoxy; and $R^6$ and $R^7$ are, independently, halo or $C_1$–$C_6$ haloalkyl; $R^8$ is $C_1$–$C_6$ alkyl; and $R^9$ and $R^{10}$, independently, are halo or $C_1$–$C_6$ haloalkyl.

The compounds having structures IA, IB, IC or II can be prepared by the reaction of a substituted phenylhydrazine with an acylating agent such as acid chloride, chloroformate, or isocyanate in the presence of a suitable base such as pyridine or triethylamine, at 0° C. to room temperature. The product of this reaction can be further acylated with an acylating agent, alkylated with an alkylating agent, oxidized with an oxidizing agent, or reacting the oxidized product with amino acid derivatives and formaldehyde. The substituted phenylhydrazine starting material can be prepared from the corresponding substituted aniline as described in U.S. Pat. No. 6,297,275.

The substituted phenoxyanilines can be prepared using the following synthetic method:

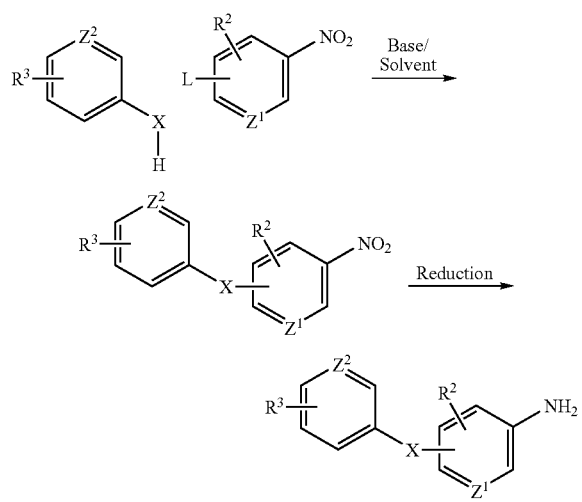

where L is a halogen.

The substituted phenylanilines can be prepared using an alternative approach as shown below:

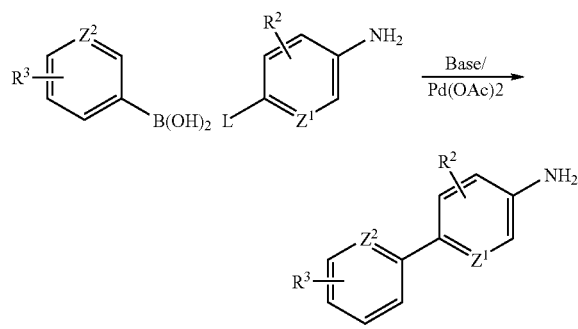

The compounds having structure (III) can be prepared by the reaction of substituted phenyldiazonium salt with nitroalkane in the presence of a suitable base such as CH$_3$CO$_2$Na and NaOH at 0° C. to room temperature as shown below:

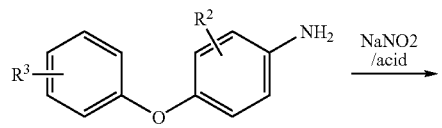

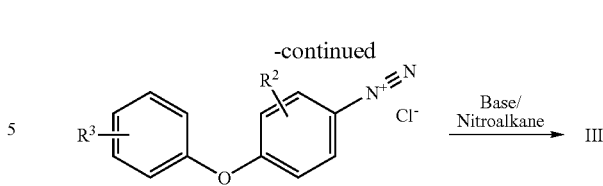

For the purposes of this invention, the term "controlling fungi" means inhibiting both future infestation and continued growth of existing infestations.

This invention also relates to a method for controlling fungi, particularly phytopathogenic fungi, comprising contacting the fungi with a fungicidally effective amount of a phenoxyphenylhydrazine compound of the formula:

a)

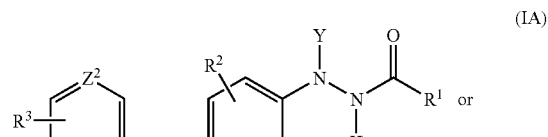
(IA)

(IB)

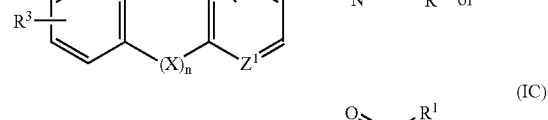
(IC)

wherein X, n, Y, Z$^1$, Z$^2$, and R$^1$–R$^4$ are as defined above;

b)

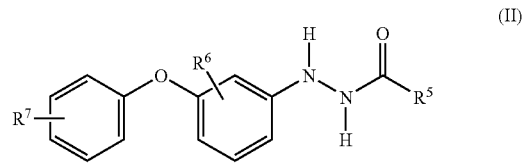
(II)

wherein R$^5$, R$^6$ and R$^7$ are as defined above; or c)

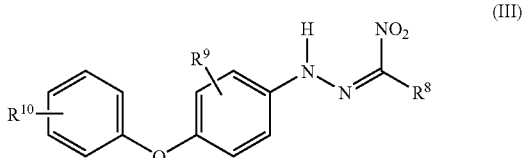
(III)

wherein R$^8$, R$^9$ and R$^{10}$ are as defined above.

Compositions useful in the method of this invention comprise (a) a fungicidally effective of a compound having a structure of formula IA, IB, IC, II, or III above, and (b) a suitable carrier. Such suitable carriers may be solid or liquid in nature.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of the resulting pesticide composition.

The compositions useful in the method of this invention can alternatively comprise solid carriers taking the form of dusts, granules, wettable powders, pastes, aerosols, emulsions, emulsifiable concentrates, and water-soluble solids.

For example, the compounds useful in the method of this invention can be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation or seed treatment, are suitably prepared using a granular or pellitized form of carrier such as granular clays, vermiculite, charcoal or corn cobs.

Alternatively, the compounds useful in the method of this invention can be applied in liquids or sprays when utilized in a liquid carrier, such as in a solution comprising a compatible solvent such as acetone, benzene, toluene or kerosene, or as dispersed in a suitable non-solvent medium, for example, water.

Another method of application to the loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For treatment of plants (such term including plant parts), the compounds useful in the method of this invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which are pesticidally active, such as insecticides, acaricides, fungicides or bactericides.

It will be understood that the amount of the compound in a given formulation useful in the method of this invention will depend upon the specific fungus to be combatted, as well as upon the specific chemical composition and formulation of the compound being employed, the method of applying the compound/formulation and the locus of treatment so that the fungicidally effective amount of the compound may vary widely. Generally, however, concentrations of the compound as the active ingredient in fungicidally effective formulations in the method of this invention can range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice and the like.

To control fungi, sprays of the compounds can be applied to the fungi directly and/or to plants or plant seeds upon which they feed or nest. The fungicidally active formulations useful in the method of this can also be applied to the soil, water, or other growth medium in which the pests are present.

The specific methods of application, as well as the selection and concentration of the compounds useful in the method of this invention, will, of course, vary depending upon such circumstances as geographic area, climate, topography, plant tolerance, etc. For specific circumstances, one skilled in the art may readily determine the proper compound, concentration and method of application by routine experimentation.

Examples of phytopathogenic fungi which can be controlled by the method of this invention include, e.g., the following:

*Erysiphe graminis* f.sp. *hordei*
*Erysiphe cichoracearum*
*Erysiphe polygoni*
*Pyricularia grisea*
*Helminthosporium sativum*
*Uromyces appendiculatus*
*Botrytis cinerea*
*Colletotrichum gossypii*
*Cercosporidium personatum*
*Fusarium nivale*
*Phytopthora infestans*
*Pythium ultimum*
*Rhizoctonia solani*
*Sclerotinia minor*
*Septoria nodurum*

The following examples are provided to illustrate the present invention.

EXAMPLES

Example 1

Preparation of 1-methylethyl 2-[4-[3-(trifluoromethyl)phenoxy]phenyl]hydrazinecarboxylate (Compound 1)

Step 1: Preparation of 1-Nitro-4-[3-(trifluoromethyl)phenoxy]benzene

A mixture of 1-chloro-4-nitrobenzene (11 g), 3-(trifluoromethyl)phenol (12 g), and potassium carbonate (21 g) in dimethyl formamide (175 mL) was heated at 120° C. for about 16 hours. The reaction mixture was cooled to room temperature and poured over ice-water. The mixture was filtered and the solid collected was washed with water and dried under vacuum (25 g).

Step 2: Preparation of 4-[3-(trifluoromethyl)phenoxy]benzenamine

To 1-Nitro-4-[3-(trifluoromethyl)phenoxy]benzene (19 g) in ethyl acetate (250 mL) was added 5% palladium on charcoal (1.5 g). The mixture was stirred under hydrogen gas for about 36 h, and then filtered through Celite. The filtrate was concentrated to yield a red oil (17 g).

Step 3: Preparation of 4-[3-(trifluoromethyl)phenoxy]phenylhydrazine hydrochloride 4-[3-(Trifluoromethyl)phenoxy]benzenamine (15 g) was added to a stirred solution of 6 M HCl (190 mL). The resulted suspension was cooled to −5° C., and then an aqueous solution of $NaNO_2$ (4.5 g in 15 mL water) was added dropwise over a period of 15 min. The reaction mixture was stirred for another 30 min, followed by the gradual addition of a solution of $SnCl_2.2H_2O$ (69 g in 100 mL conc HCl). After stirring at −5° C. for 2 h, the stirred mixture was warmed to room temperature overnight, filtered, and the collected solid was washed with 6 M HCl, water, and dried (18 g).

Step 4: Preparation of 1-methylethyl 2-[4-[3-(trifluoromethyl)phenoxy]phenyl]-hydrazinecarboxylate (Compound 1)

To a suspension of 4-[3-(trifluoromethyl)phenoxy]phenylhydrazine hydrochloride (11 g) and pyridine (6.0 mL) in ethyl acetate (100 mL) at 0° C. was added dropwise isopropyl chloroformate (38 mL, 1M in toluene) over a period of 30 min. The mixture was then stirred at room temperature for 5 hour, quenched with 1M aqueous HCl (100 mL). The organic layer was separated, washed twice with water (100 mL), dried over anhydrous sodium sulfate, and finally evaporated under reduced pressure to yield a light brown solid (11 g).

Example 2

Preparation of 1-methylethyl 2-(trifluoroacetyl)-2-[4-[3-(trifluoromethyl)phenoxy]phenyl]-hydrazine carboxylate (Compound 2)

To the product (0.4 g) of Step 4 of Example 1 was added dichloromethane (10 mL) and trifluoroacetic anhydride (1 mL). The solution was stirred at room temperature for 4 hours and then concentrated to give an oily residue, which upon co-evaporation with toluene (2×10 mL) under reduced pressure, gave a brown solid (0.5 g).

Example 3

Preparation of 1-methylethyl 2-methyl-2-[4-[3-(trifluoromethyl)phenoxy]phenyl]hydrazine carboxylate (Compound 3)

The product (0.4 g) of Step 4 of Example 1 was heated in methyl iodide (5 mL) at reflux for 1 day and then concentrated under reduced pressure to give a red oil (0.5 g).

Example 4

Preparation of N'-{3-fluoro-4-[3-(trifluoromethyl)phenoxy]phenyl}acetohydrazide (Compound 7)

To [3-fluoro-4-[3-(trifluoromethyl)phenoxy]phenyl]hydrazine hydrochloride (0.35 g) prepared using the method described in Example 1, in ethyl acetate (5 mL), was added pyridine (0.24 mL) at −10° C. After dropwise addition of acetyl chloride (0.1 mL), the mixture was stirred for 3 h and then acidified with 6 M HCl. Water was added, and the product was extracted with ether. The organic layer was separated, dried, and concentrated. The residue was purified by column chromatography on silica (using dichloromethane, followed by 5:1 dichloromethane:ether as eluants) to give a solid (0.2 g).

Example 5

Preparation of isopropyl 2-[2-fluoro-3'-(trifluoromethyl)-1,1'-biphenyl-4-yl]hydrazine-carboxylate (Compound 8)

Step 1: Preparation of 2-fluoro-3'-(trifluoromethyl)-1,1'-biphenyl-4-amine

A mixture of 4-bromo-3-fluoroaniline (4.3 g), 3-trifluoromethylphenylboronic acid (4.4 g), sodium carbonate (6.5 g), palladium(II) acetate (0.22 g) and 2-(di-t-butylphosphino)biphenyl (0.60 g) were weighed into a reaction tube and flushed with nitrogen. A 70:30 mixture of dioxane/water (50 mL) was then added and the mixture was heated at 90° C. for 16 h. Ethyl acetate and water was added and the phases separated. The organic phase was dried and concentrated. The residue was purified by column chromatography on silica to give a solid (2.5 g).

Step 2: Preparation of isopropyl 2-[2-fluoro-3'-(trifluoromethyl)-1,1'-biphenyl-4-yl]-hydrazinecarboxylate (Compound 8)

The procedures described in Steps 3 and 4 of Example 1 were used to prepare Compound 8.

Example 6

Preparation of 1-methylethyl [4-[3-(trifluoromethyl)phenoxy]phenyl]diazene carboxylate (Compound 9)

To the product (0.42 g) of Step 4 of Example 1 was added dichloromethane (10 mL) and 5% aqueous sodium hypochlorite (20 mL). The two-phase mixture was stirred vigorously overnight at room temperature, the organic layer was separated, dried over anhydrous sodium sulfate, and concentrated under reduced pressure to give a red oil (0.4 g).

Example 7

Preparation of 1-methylethyl 2-[3-fluoro-4-[3-(trifluoromethyl)phenoxy]phenyl]-4-methyl-1,2,4-triazolidine-1-carboxylate (Compound 10)

1-Methylethyl 3-fluoro-4-[3-(trifluoromethylphenoxy)phenyl]diazenecarboxylate (370 mg) prepared using the procedure described in Example 6, sarcosine (178 mg) and paraformaldehyde (150 mg) were suspended in toluene (10 mL) and the reaction mixture was then heated at reflux for 3 hours. Solvent was then removed under reduced pressure and the residue was purified by chromatography on silica to give a colorless oil (120 mg).

Example 8

Preparation of 1-{3-fluoro-4-[3-(trifluoromethyl)phenoxy]phenyl}-2-(1-nitropropylidene)-hydrazine (Compound 12)

A mixture of 3-fluoro-4-[3-(trifluoromethyl)phenoxy] aniline (1.35 g) prepared as described in Step 2 of Example 1, water (18.2 mL), and conc. HCl (1.5 mL) was stirred overnight at room temperature. The suspension mixture was cooled to −5° C. and was added dropwise of $NaNO_2$ (0.36 g in 2 mL water) over a period of about 10 min. The reaction mixture was further stirred for 30 minutes, and added $CH_3CO_2Na3H_2O$ (6.6 g). The resulting salt was added to a previously prepared solution of nitropropane (0.44 g) and NaOH (0.20 g) in ethanol (8 mL) and water (2 mL). The resulting mixture was stirred at 0° C. and then at room temperature overnight. It was filtered to give a red solid that was subsequently purified by column chromatography on silica (40% dichloromethane/hexane).

The remaining compounds listed in Tables 1A and 1B (i.e., Compounds 4–6, and 11) were prepared according to the procedures described for the foregoing Examples 1–8 using the correspondingly different substituted phenylhydrazine. The identity of each of the compounds is confirmed by NMR spectroscopy.

TABLE 1B

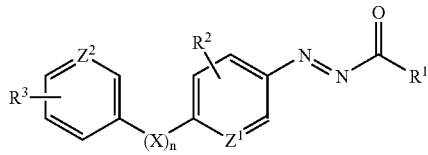

| Cmpd | X | n | $R^1$ | $R^2$ | $R^3$ | $Z^1$ | $Z^2$ | $^1$H NMR data ($CDCl_3$) |
|---|---|---|---|---|---|---|---|---|
| 9 | O | 1 | $OCH(CH_3)_2$ | H | 3-$CF_3$ | C | C | d (6) 1.5 |
|   |   |   |   |   |   |   |   | sp (1) 5.3 |
|   |   |   |   |   |   |   |   | dd (2) 7.1 |
|   |   |   |   |   |   |   |   | m (4) 7.3–7.6 |
|   |   |   |   |   |   |   |   | dd (2) 8.0 |

TABLE 1A

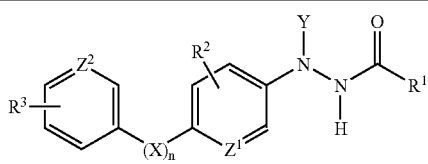

| Cmpd. | X | Y | n | $R^1$ | $R^2$ | $R^3$ | $Z^1$ | $Z^2$ | $^1$H NMR data ($CDCl_3$) |
|---|---|---|---|---|---|---|---|---|---|
| 1 | O | H | 1 | $OCH(CH_3)_2$ | H | 3-$CF_3$ | C | C | d (6) 1.3; sp (1) 5.0; br s (1) 5.8; br s (1) 6.5; m (8) 6.8–7.4 |
| 2 | O | $CF_3CO$ | 1 | $OCH(CH_3)_2$ | H | 3-$CF_3$ | C | C | d(6) 1.3; sp (1) 5.0; m (9) 6.9–7.5 |
| 3 | O | $CH_3$ | 1 | $OCH(CH_3)_2$ | H | 3-$CF_3$ | C | C | m (6) 1.3; s (3) 3.2; sp (1) 5.0; br s (1) 6.5; m (8) 6.9–7.5 |
| 4 | S | $CF_3CO$ | 1 | $OCH(CH_3)C_2H_5$ | H | H | C | C | m (8) 0.8–1.8; sx (1) 4.8; m (10) 7.1–7.5 |
| 5 | O | H | 1 | $OCH_3$ | H | H | C | N | s (3) 3.8; br s (1) 6.2; m (7) 6.8–7.7; m (2) 8.2–8.5 |
| 6 | O | $CF_3CO$ | 1 | $OCH(CH_3)_2$ | H | 3-Cl | N | C | d (6) 1.3; sp (1) 5.0; m (6) 6.9–7.4; br s (1) 7.9; d (1) 8.3 |
| 7 | O | H | 1 | $CH_3$ | 3-F | 3-$CF_3$ | C | C | s (3) 2.1; d (1) 5.9; m (2) 6.7; m (8) 7.0–7.4 |
| 8 | — | H | 0 | $OCH(CH_3)_2$ | 3-F | 3-$CF_3$ | C | C | d (6) 1.3; sp (1) 5.0; br s (1) 5.3; br s (1) 6.5; m (2) 6.7; m (5) 7.3–7.8 |

TABLE 1C

[Structure: R³-(Z²)-phenyl-(X)ₙ-phenyl(R²)(Z¹)-N(R¹C(O))-N(CH₃)-CH₂ triazolidine]

| Cmpd | X | n | R¹ | R² | R³ | Z¹ | Z² | ¹H NMR data (CDCl₃) |
|---|---|---|---|---|---|---|---|---|
| 10 | O | 1 | OCH(CH₃)₂ | 3-F | 3-CF₃ | C | C | dd (6) 1.3<br>s (3) 2.5<br>m (4) 4.1–4.3<br>sp (1) 5.1<br>m (7) 6.6–7.4 |

TABLE 1D

[Structure with R⁷-phenyl-O-phenyl(R⁶)-NH-NH-C(O)-R⁵]

| Compound No. | R⁵ | R⁶ | R⁷ | ¹H NMR data (CDCl₃) |
|---|---|---|---|---|
| 11 | OCH(CH₃)₂ | 3-F | 3-CF₃ | d (6) 1.3;<br>sp (1) 5.0;<br>br s (1) 5.8;<br>m (4) 6.2–6.4;<br>m (4) 7.2–7.5 |

TABLE 1E

[Structure with R¹⁰-phenyl-O-phenyl(R⁹)-NH-N=C(R⁸)(NO₂)]

| Compound No. | R⁸ | R⁹ | R¹⁰ | ¹H NMR data (CDCl₃) |
|---|---|---|---|---|
| 12 | CH₂CH₃ | 3-F | 3-CF₃ | t (3) 1.3;<br>q (2) 2.9;<br>m (7) 7.0–7.4;<br>br s (1) 12.1 |

Biological Tests

Foliar Spray for the Control of Barley Powdery Mildew caused by *Erysiyphe graminis* f.sp. *hordei*

Technical grade material at defined ppm rates (w/v) in an acetone:water mixture (1:9) containing 0.1% Tween 20 (v/v) is sprayed to near run-off onto 7-days-old greenhouse-grown barley plants (var. "Robust") at the cotyledon stage. Treated plants are inoculated within 24 hours by brushing mildew-infected plants over the treated plants. Inoculated plants are kept in the greenhouse for 6–8 days for disease development. Disease severity is examined and the % control is calculated as [% disease on untreated plants–% disease on treated plants]/% diseases in untreated plants. The results of these tests are shown in Table 2A below under the heading "Foliar Application—Barley Powdery Mildew".

Foliar Spray for the Control of Bean Powdery Mildew Caused by *Erysiyphe polygoni*

Technical grade material at defined ppm rates (w/v) in an acetone:water mixture (1:9) containing 0.1% Tween 20 (v/v) is sprayed to near run-off onto greenhouse-grown Pinto bean plants (var. "Othello") in the second leaf stage. Treated plants are inoculated within 24 hours by brushing mildew-infected plants over treated plants. Inoculated plants are kept in the greenhouse for two weeks for disease development. Disease severity is examined and the % control is calculated as [% disease on untreated plants–% disease on treated plants]/% disease on untreated plants. The results of these tests are shown in Table 2A below under the heading "Foliar Application—Bean Powdery Mildew".

Foliar Spray for the Control of Barley Blotch Caused by *Helminthosporium sativum*

Technical grade material at defined ppm rates (w/v) in an acetone:water mixture (1:9) containing 0.1% Tween 20 (v/v) is sprayed to near run-off onto 7-days-old greenhouse-grown barley plants (var. "Robust") at the cotyledon stage. Treated plants are inoculated within 24 hours from spraying with an aqueous suspension of approximately 15,000 conidia/ml of *Helminthosporium sativum* grown on artificial medium. Inoculated plants are placed into a high humidity chamber for 24 hr and then transferred to the greenhouse for 4–5 days for disease development. Disease severity is examined and the % control is calculated as [% disease on untreated plants–% disease on treated plants]/% disease on untreated plants.

The results of these tests are shown in Table 2A below under the heading "Foliar Application—Barley Blotch".

Foliar Spray for the Control of Rice Blast Caused by *Pyricularia oryzae*

Technical grade material at defined ppm rates (w/v) in an acetone:water mixture (1:9) containing 0.1% Tween 20 (v/v) is sprayed to near run-off onto 7-days-old greenhouse-grown rice plants (var. "Lemont") at the cotyledon stage. Treated plants are inoculated within 24 hours with an aqueous suspension of approximately 45,000 conidia/ml of *Pyricularia oryzae* grown on artificial medium. Inoculated plants are placed into a high humidity chamber for 48 hr and then transferred to the greenhouse for 4–5 days for disease development. Disease severity is examined and the % control is calculated as [% disease on untreated plants–% disease on treated plants]/% disease on untreated plants. The results of these tests are shown in Table 2A below under the heading "Foliar Application—Rice Blast".

Foliar Spray for the Control of Geranium Gray Mold Caused by *Botrytis cinerea*

Technical grade material at defined ppm rates (w/v) in an acetone:water mixture (1:9) containing 0.1% Tween 20 (v/v) is sprayed to near run-off onto mature greenhouse-grown geranium plants (var. "Pinto White") in the second leaf stage. Treated plants are inoculated within 24 hours with an aqueous suspension of approximately 100,000 conidia/ml of *Botrytis cinerea* grown on artificial medium. Inoculated plants are placed into a high humidity chamber for 5 days and then transferred to the greenhouse for one day for disease development. Disease severity is examined and the % control is calculated as [% disease on untreated plants–% disease on treated plants]/% disease on untreated plants. The results of these tests are shown in Table 2A below under the heading "Foliar Application—Geranium Gray Mold".

Foliar Spray for the Control of Tomato Late Blight Caused by *Phytophthora infestans*

Technical grade material at defined ppm rates (w/v) in an acetone:water mixture (1:9) containing 0.1% Tween 20 (v/v) is sprayed to near run-off onto 2-weeks-old greenhouse-grown tomato plants (var. "Patio") in the second leaf stage. Treated plants are inoculated within 24 hours with an aqueous suspension of approximately 50,000 sporangia/ml of *Phytophthora infestans* grown on artificial medium. Inoculated plants are placed into a high humidity chamber for 4 days and then transferred to the greenhouse for one day for disease development. Disease severity is examined and the % control is calculated as [% disease on untreated plants−% disease on treated plants]/% disease on untreated plants. The results of these tests are shown in Table 2A below under the heading "Foliar Application—Tomato Late Blight".

Foliar Spray for the Control of Bean Rust Caused by *Uromyces appendiculatus*

Technical grade material at defined ppm rates (w/v) in an acetone:water mixture (1:9) containing 0.1% Tween 20 (v/v) is sprayed to near run-off onto 10-days-old greenhouse-grown Pinto bean plants (var. "Othello") in the second leaf stage. Treated plants are inoculated within 24 hours with an aqueous suspension of approximately 20,000 uredospores of *Uromyces appendiculatus* harvested from rust-infected plants. Inoculated plants are placed into a high humidity chamber for 24 hr and then transferred to the greenhouse for two weeks for disease development. Disease severity is examined and the % control is calculated as [% disease on untreated plants−% disease on treated plants]/% disease on untreated plants. The results of these tests are shown in Table 2A below under the heading "Foliar Application—Bean Rust".

Soil Drench for the Control of Barley or Cucumber Powdery Mildew

Technical grade material formulated as described for foliar sprays is dispensed at defined rates (ml/$cm^3$) into the soil in the pots for barley and cucumber in the stages as described for the foliar sprays. Treated plants are inoculated, within 24 hours with the respective powdery mildew species as described for the foliar spray tests. Inoculated plants are kept in the greenhouse for 6–8 days for disease development. Disease severity is examined and the % control is calculated as [% disease on untreated plants−% disease on treated plants]/% disease on untreated plants. The results of these tests are shown in Table 2B below under the heading "Drench Application—Barley Powdery Mildew" and "Drench Application—Cucumber Powdery Mildew".

In Vitro Evaluation

Technical grade material solubilized in acetone at 3000 ppm w/v and diluted in distilled water is delivered in aliquots of at least 10 ul into 100 to 200 ul of a standard fungal growth medium in 96 well plates to provide final rates of 10–100 ppm a.i. (w/v). Each well is inoculated with at least 100 conidia and/or mycelial fragments of fungal pathogens such as *Phthium ultimum, Phytophthora infestans, Rhizoctonia solani, Fusarium nivale, Botrytis cinerea, Colletotrichum gossypii, Cercosporidium personatum, Sclerotinia minor*, or *Sclerotium rolfsii*. After 48 hours, the growth density is assessed to determine the % inhibition as [density in untreated well−density in treated well]/density in untreated well. The results of these tests are located in Tables 3A and 3B.

TABLE 2A

Percent (%) disease control of phenylhydrazine fungicides at 300 ppm in greenhouse foliar application assays

| | Foliar Application (Percent Control) | | | | | | |
|---|---|---|---|---|---|---|---|
| Cmpd. No. | Barley Powdery Mildew | Barley Blotch | Rice Blast | Bean Powdery Mildew | Bean Rust | Tomato Late Blight | Geranium Gray Mold |
| 1 | 90 | 97 | 79 | — | 97 | 12 | 87 |
| 2 | 25 | 99 | 15 | — | 0 | — | — |
| 3 | 62 | 0 | 10 | — | 0 | — | 87 |
| 4 | 0 | 0 | — | 88 | 0(e) | 0 | — |
| 5 | 0 | 0 | — | 0 | 0(e) | — | — |
| 6 | 0 | 97 | 92 | — | 0 | 0 | 82 |
| 7 | 80 | 80 | 0 | — | — | 0 | 80 |
| 8 | 0 | 98 | 70 | — | — | 0 | 90 |
| 9 | 15 | 97 | 98 | — | 45 | — | — |
| 10 | 100 | 90 | 0 | — | — | — | 0 |
| 11 | 85 | 0 | 0 | — | — | 0 | 0 |
| 12 | 80 | 0 | 0 | — | — | 0 | 0 |

(e)screened against rust on beans as foliar-applied eradicant.

TABLE 2B

Percent (%) disease control of phenylhydrazine fungicides at 300 ppm in greenhouse drench application assays

| | Drench Application (Percent Control) | |
|---|---|---|
| Compound No. | Barley Powdery Mildew | Cucumber Powdery Mildew |
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | — | — |
| 8 | — | — |
| 9 | 25 | 0 |
| 10 | — | — |
| 11 | — | — |
| 12 | — | — |

TABLE 3A

Percent (%) control of phytopathogenic fungi by phenylhyrazine derivatives in vitro.

| Cmpd No. | Rate (ppm) | Percent Control | | | | |
|---|---|---|---|---|---|---|
| | | *Botrytis cinerea* | *Colletotricum gossypii* | *Cercosporidium personatum* | *Fusarium nivale* | *Phytophthora infestants* |
| 1 | 100 | 100 | — | — | 29 | 100 |
| 2 | 100 | 90 | — | — | 20 | 100 |
| 3 | 50 | 100 | — | — | 82 | 79 |
| 4 | 100 | 75 | 15 | 65 | 50 | 100 |
| 5 | 100 | 25 | 100 | 0 | 90 | 20 |
| 6 | 100 | 98 | — | — | 71 | 100 |
| 7 | 10 | 30 | — | — | 8 | 0 |
| 8 | 10 | 63 | — | — | 22 | 18 |
| 9 | 100 | 77 | — | — | 75 | 9 |
| 10 | 100 | 0 | — | — | 0 | 0 |
| 11 | 10 | 0 | — | — | 18 | 0 |
| 12 | 10 | 18 | — | — | 20 | 0 |

TABLE 3B

Percent (%) control of phytopathogenic fungi by phenylhyrazine derivatives in vitro.

| Compound No. | Rate (ppm) | Percent Control | | | |
|---|---|---|---|---|---|
| | | *Pythium ultimum* | *Rhizoctonia solani* | *Sclerotinia minor* | *Sclerotium rolfsii* |
| 1 | 100 | 100 | 91 | — | 100 |
| 2 | 100 | 100 | 82 | — | 67 |
| 3 | 50 | 100 | 63 | — | — |
| 4 | 100 | 15 | 95 | 50 | — |
| 5 | 100 | 70 | 0 | 100 | 100 |
| 6 | 100 | 25 | 100 | — | 98 |
| 7 | 10 | 8 | 80 | — | — |
| 8 | 10 | 26 | 58 | — | — |
| 9 | 100 | 0 | 22 | — | 91 |
| 10 | 100 | 0 | 79 | — | — |
| 11 | 10 | 9 | 4 | — | — |
| 12 | 10 | 3 | 68 | — | — |

What is claimed is:

1. A phenoxyphenylhydrazine compound of the formula:

a)

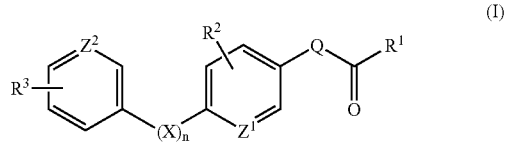

(I)

wherein
Q is —NY—NH—, —N=N—, or

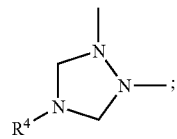

X is oxygen, sulfoxide, or sulfone;
n is 1;

Y is hydrogen, $C_1$–$C_4$ alkanoyl, $C_1$–$C_4$ haloalkanoyl, $C_1$–$C_6$ straight chain alkoxycarbonyl, $C_1$–$C_4$ alkoxy($C_1$–$C_4$)alkoxycarbonyl, $C_1$–$C_4$ alkyl, or $C_1$–$C_4$ haloalkyl;

$R^1$ is $C_1$–$C_6$ alkoxy, $C_3$–$C_6$ branched alkoxy, $C_3$–$C_6$ cycloalkoxy, phenoxy, benzyloxy, $C_2$–$C_6$ alkenyloxy, $C_2$–$C_6$ alkynyloxy, $C_1$–$C_6$ haloalkoxy, silyloxy, ($C_1$–$C_6$ alkoxy)-carbonylmethoxy, $C_1$–$C_6$ thioalkoxy, $C_1$–$C_6$ alkylamino, $C_1$–$C_6$ alkyl, $C_3$–$C_6$ branched alkyl, or ($C_1$–$C_6$ alkoxy)$C_1$–$C_6$alkoxy;

$R^2$ and $R^3$ are each, independently, hydrogen, halogen, $C_1$–$C_6$ alkyl, $C_3$–$C_6$ branched alkyl, $C_1$–$C_6$ haloalkyl, $C_1$–$C_6$ alkoxy, $C_1$–$C_6$ haloalkoxy, cyano, or ($C_1$–$C_6$ alkoxy)carbonyl;

$R^4$ is $C_1$–$C_6$ alkyl; and $Z^1$ and $Z^2$ are each independently, carbon or nitrogen, with the proviso that when $Z^1$ is carbon, X is oxygen, and $R^2$ is hydrogen, then $R^3$ cannot be hydrogen; or

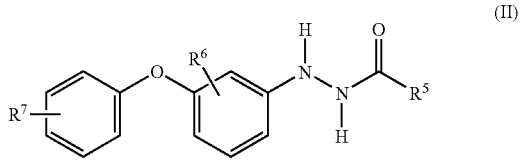

(II)

b)

wherein $R^5$ is $C_1$–$C_6$ alkoxy; and $R^6$ and $R^7$ are, independently, halo or $C_1$–$C_6$ haloalkyl.

2. A compound as recited in claim 1 having the formula:

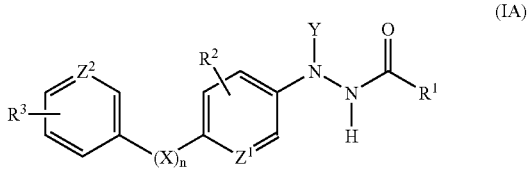

(IA)

wherein X, n, Y, $Z^1$, $Z^2$, and $R^1$–$R^2$ are as defined in claim 1.

3. A compound as recited in claim 1 having the formula:

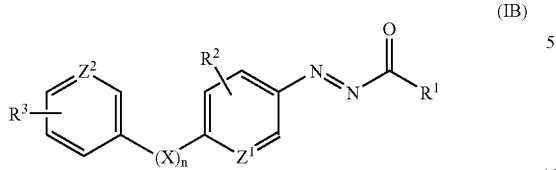
(IB)

wherein X, n, $Z^1$, $Z^2$, and $R^1$–$R^3$ are as defined in claim 1.

4. A compound as recited in claim 1 having the formula:

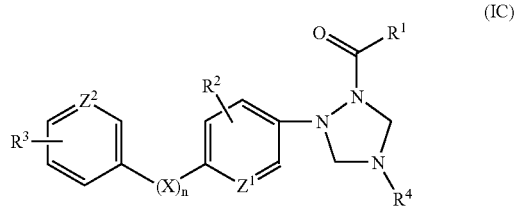
(IC)

wherein X, n, $Z^1$, $Z^2$, and $R^1R^4$ are as defined in claim 1.

5. A compound as recited in claim 1 having the formula:

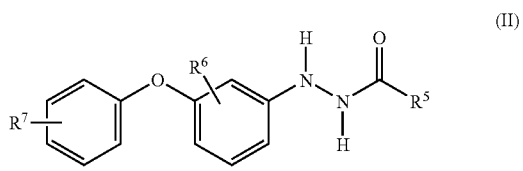
(II)

wherein $R^5$, $R^6$, and $R^7$ are as recited in claim 1.

6. A method for controlling fungi comprising contacting the fungi with a fungicidally effective amount of a phenoxyphenylhydrazine compound of the formula:

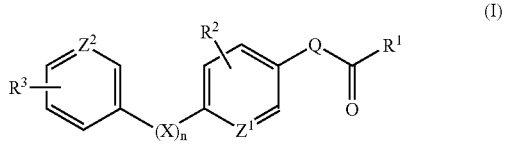
(I)

a) wherein
Q is —NY—NH—, —N=N—, or

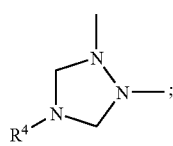

X is oxygen, sulfur, sulfoxide, or sulfone;
n is 0 or 1;
Y is hydrogen, $C_1$–$C_4$ alkanoyl, $C_1$–$C_4$ haloalkanoyl, $C_1$–$C_6$ straight chain or branched alkoxycarbonyl, $C_1$–$C_4$ alkoxy($C_1$–$C_4$)alkoxycarbonyl, $C_1$–$C_4$ alkyl, or $C_1$–$C_4$ haloalkyl;
$R^1$ is $C_1$–$C_6$ alkoxy, $C_3$–$C_6$ branched alkoxy, $C_3$–$C_6$ cycloalkoxy, phenoxy, benzyloxy, $C_2$–$C_6$ alkenyloxy, $C_2$–$C_6$ alkynyloxy, $C_1$–$C_6$ haloalkoxy, silyloxy, ($C_1$–$C_6$ alkoxy)-carbonylmethoxy, $C_1$–$C_6$ thioalkoxy, $C_1$–$C_6$ alkylamino, $C_1$–$C_6$ alkyl, $C_3$–$C_6$ branched alkyl, ($C_1$–$C_6$ alkoxy)$C_1$–$C_6$ alkoxy, or ($C_1$–$C_6$ alkoxy)carbonyl;
$R^2$ and $R^3$ are each, independently, hydrogen, halogen, $C_1$–$C_6$ alkyl, $C_3$–$C_6$ branched alkyl, $C_1$–$C_6$ haloalkyl, $C_1$–$C_6$ alkoxy, $C_1$–$C_6$ haloalkoxy, cyano, or ($C_1$–$C_6$ alkoxy)carbonyl;
$R^4$ is $C_1$–$C_6$ alkyl; and
$Z^1$ and $Z^2$ are each independently, carbon or nitrogen,
with the proviso that when $Z^1$ is carbon, X is oxygen, and $R^2$ is hydrogen, then $R^3$ cannot be hydrogen; or

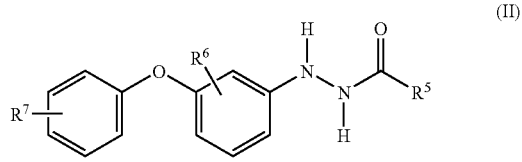
(II)

b)
wherein $R^5$ is $C_1$–$C_6$ alkoxy; and $R^6$ and $R^7$ are, independently, halo or $C_1$–$C_6$ haloalkyl.

7. A method as recited in claim 6 comprising contacting the fungi with a fungicidally effective amount of a compound having the formula:

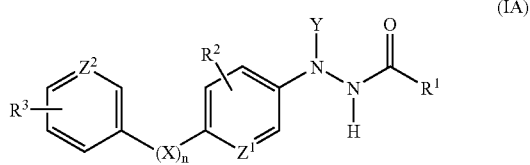
(IA)

wherein X, n, Y, $Z^1$, $Z^2$, and $R^1$–$R^3$ are as defined in claim 6.

8. A method as recited in claim 4 comprising contacting the fungi with a fungicidally effective amount of a compound having the formula:

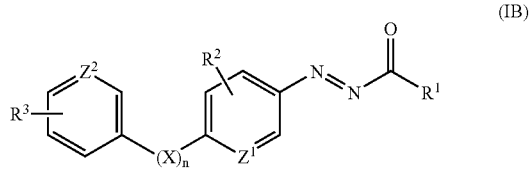
(IB)

wherein X, n, $Z^1$, $Z^2$, and $R^1$–$R^3$ are as defined in claim 6.

9. A method as recited in claim 6 comprising contacting the fungi with a fungicidally effective amount of a compound having the formula:

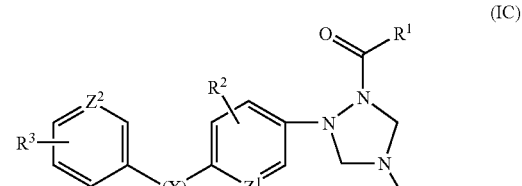
(IC)

wherein X, n, $Z^1$, $Z^2$, and $R^1$–$R^4$ are as defined in claim 6.

10. A method as recited in claim 6 comprising contacting the fungi with a fungicidally effective amount of a compound having the formula:

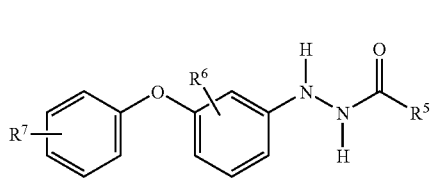
(II)

wherein $R^5$, $R^6$, and $R^7$ are as recited in claim 6.

11. A method for controlling fungi on a plant or plant seed which comprises applying to the plant or the plant seed, or to a growth medium or water in which the plant or plant seed is growing or is to be grown in, a fungicidally effective amount of a compound of the formula:

a)

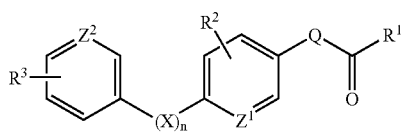
(I)

wherein Q is —NY—NH—, —N=N—, or

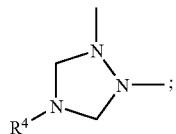

X is oxygen, sulfur, sulfoxide, or sulfone;
n is 0 or 1;
Y is hydrogen, $C_1$–$C_4$ alkanoyl, $C_1$–$C_4$ haloalkanoyl, $C_1$–$C_6$ straight chain or branchd alkoxycarbonyl, $C_1$–$C_4$ alkoxy($C_1$–$C_4$)alkoxycarbonyl, $C_1$–$C_4$ alkyl, or $C_1$–$C_4$ haloalkyl;
$R^1$ is $C_1$–$C_6$ alkoxy, $C_3$–$C_6$ branched alkoxy, $C_3$–$C_6$ cycloalkoxy, phenoxy, benzyloxy, $C_2$–$C_6$ alkenyloxy, $C_2$–$C_6$ alkynyloxy, $C_1$–$C_6$ haloalkoxy, silyloxy, ($C_1$–$C_6$ alkoxy)-carbonylmethoxy, $C_1$–$C_6$ thioalkoxy, $C_1$–$C_6$ alkylamino, $C_1$–$C_6$ alkyl, $C_3$–$C_6$ branched alkyl, ($C_1$–$C_6$ alkoxy) $C_1$–$C_6$ alkoxy, or ($C_1$–$C_6$ alkoxy)carbonyl;
$R^2$ and $R^3$ are each, independently, hydrogen, halogen, $C_1$–$C_6$ alkyl, $C_3$–$C_6$ branched alkyl, $C_1$–$C_6$ haloalkyl, $C_1$–$C_6$ alkoxy, $C_1$–$C_6$ haloalkoxy, cyano, or ($C_1$–$C_6$ alkoxy)carbonyl;
$R^4$ is $C_1$–$C_6$ alkyl; and
$Z^1$ and $Z^2$ are each independently, carbon or nitrogen,
with the proviso that when $Z^1$ is carbon, X is oxygen, and $R^2$ is hydrogen, then $R^3$ cannot be hydrogen; or
b)

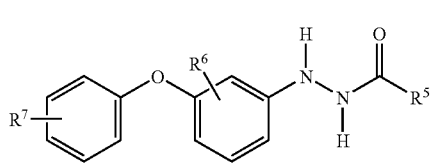
(II)

wherein $R^5$ is $C_1$–$C_6$ alkoxy; and $R^6$ and $R^6$ are, independently, halo or $C_1$–$C_6$ haloalkyl.

12. A phenoxyphenylhydrazine compound of the formula:

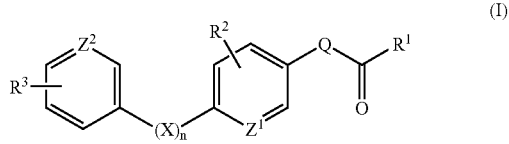
(I)

wherein
Q is —NY—NH—, —N=N—, or

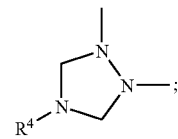

X is sulfur;
n is 1;
Y is hydrogen, $C_1$–$C_4$ alkanoyl, $C_1$–$C_4$ haloalkanoyl, $C_1$–$C_6$ straight chain or branched alkoxycarbonyl, $C_1$–$C_4$ alkoxy($C_1$–$C_4$)alkoxycarbonyl, $C_1$–$C_4$ alkyl, or $C_1$–$C_4$ haloalkyl;
$R^1$ is $C_1$–$C_6$ alkoxy, $C_3$–$C_6$ branched alkoxy, $C_3$–$C_6$ cycloalkoxy, phenoxy, benzyloxy, $C_2$–$C_6$ alkenyloxy, $C_2$–$C_6$ alkynyloxy, $C_1$–$C_6$ haloalkoxy, silyloxy, ($C_6$–$C_6$ alkoxy)-carbonylmethoxy, $C_1$–$C_6$ thioalkoxy, $C_1$–$C_6$ alkylamino, ($C_1$–$C_6$ alkoxy) $C_1$–$C_6$ alkoxy, or ($C_1$–$C_6$ alkoxy)carbonyl;
$R^2$ and $R^3$ are each, independently, hydrogen, halogen, $C_1$–$C_6$ haloalkyl, $C_1$–$C_6$ alkoxy, $C_1$–$C_6$ haloalkoxy, cyano, or ($C_1$–$C_6$ alkoxy)carbonyl;
$R^4$ is $C_1$–$C_6$ alkyl; and
$Z^1$ and $Z^2$ are each independently, carbon or nitrogen.

13. A phenoxyphenylhydrazine compound as recited in claim 12 having the formula:

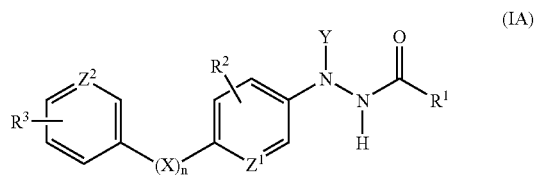
(IA)

wherein X, n, Y, $Z^1$, $Z^2$, and $R^1$–$R^3$ are as defined in claim 12.

14. A phenoxyphenylhydrazine compound of the formula:

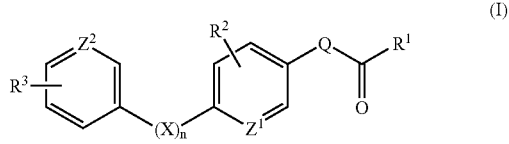
(I)

wherein
Q is —NY—NH—, —N=N—, or

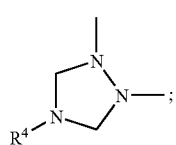
n is 0;
Y is hydrogen, $C_1$–$C_4$ alkanoyl, $C_1$–$C_4$ haloalkanoyl, $C_1$–$C_4$ alkyl, or $C_1$–$C_4$ haloalkyl;
$R^1$ is $C_1$–$C_6$ alkoxy, $C_3$–$C_6$ branched alkoxy, $C_3$–$C_6$ cycloalkoxy, phenoxy, benzyloxy, or $C_2$–$C_6$ alkynyloxy;
$R^2$ and $R^3$ are each, independently, hydrogen, halogen, $C_1$–$C_6$ haloalkyl, $C_1$–$C_6$ alkyl, or $C_1$–$C_6$ alkoxy;
$R^4$ is $C_1$–$C_6$ alkyl; and
$Z^1$ and $Z^2$ are carbon.
\* \* \* \* \*